(12) United States Patent
Ewais et al.

(10) Patent No.: US 10,081,060 B2
(45) Date of Patent: Sep. 25, 2018

(54) METHOD OF FORMING SILVER NANOPARTICLES AND A USE THEREOF

(71) Applicant: King Abdulaziz University, Jeddah (SA)

(72) Inventors: Hassan Amroun Ewais, Jeddah (SA); Iqbal Mohamed Ismail, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/065,076

(22) Filed: Mar. 9, 2016

(65) Prior Publication Data

US 2017/0259341 A1    Sep. 14, 2017

(51) Int. Cl.

| | | |
|---|---|---|
| *B82Y 40/00* | (2011.01) | |
| *B22F 9/24* | (2006.01) | |
| *A61K 8/04* | (2006.01) | |
| *A61Q 19/00* | (2006.01) | |
| *A61K 9/10* | (2006.01) | |
| *A61K 33/38* | (2006.01) | |
| *A61K 9/16* | (2006.01) | |
| *A61K 8/19* | (2006.01) | |
| *B01J 23/50* | (2006.01) | |
| *B01J 35/00* | (2006.01) | |
| *B22F 1/00* | (2006.01) | |
| *B82Y 5/00* | (2011.01) | |

(52) U.S. Cl.
CPC .................. *B22F 9/24* (2013.01); *A61K 8/04* (2013.01); *A61K 8/19* (2013.01); *A61K 9/10* (2013.01); *A61K 9/1688* (2013.01); *A61K 33/38* (2013.01); *A61Q 19/00* (2013.01); *B01J 23/50* (2013.01); *B01J 35/0013* (2013.01); *B22F 1/0044* (2013.01); *B22F 1/0048* (2013.01); *A61K 2800/10* (2013.01); *A61K 2800/413* (2013.01); *A61K 2800/805* (2013.01); *B22F 2009/245* (2013.01); *B22F 2301/255* (2013.01); *B22F 2304/054* (2013.01); *B22F 2998/10* (2013.01); *B82Y 5/00* (2013.01); *B82Y 40/00* (2013.01)

(58) Field of Classification Search
None
See application file for complete search history.

(56) References Cited

U.S. PATENT DOCUMENTS

| | | | | |
|---|---|---|---|---|
| 2006/0083694 | A1* | 4/2006 | Kodas | B01J 13/0043 424/46 |
| 2010/0172997 | A1* | 7/2010 | Omary | A61K 9/5115 424/489 |
| 2010/0272770 | A1* | 10/2010 | De Windt | A01N 59/16 424/411 |
| 2011/0303885 | A1* | 12/2011 | Vanheusden | H01B 1/22 252/513 |
| 2011/0313059 | A1* | 12/2011 | Blosi | B01J 13/0043 516/97 |
| 2015/0118496 | A1 | 4/2015 | Cho et al. | |

FOREIGN PATENT DOCUMENTS

| | | |
|---|---|---|
| EP | 2 789 235 A1 | 10/2014 |
| WO | WO 2010/010569 A1 | 1/2010 |
| WO | WO 2010/100107 A2 | 9/2010 |

OTHER PUBLICATIONS

M. Nadagouda, et al., "Microwave-Assisted Green Synthesis of Silver Nanostructures," Accounds of Chemical Research, vol. 44, No. 7, 2011, 469-478.*
R. M. El-Shishtawy et al., "Synthesis and spectroscopic studies of stable aqueous dispersion of silver nanoparticles," Spectrochimica Acta Part A 79 (2001) 1505-1510.*
Germán Ayala Valencia, et al., "A Simple and Green Method for Synthesis of Ag and Au Nanoparticles Using Biopolymers and Sugars as Reducing Agents", Nanotechnology Biosensors Devices Laboratory, Materials Research Society, MRS, Symposium D11.3, 2011, 23 pages.
Aleš Panáček, et al., "Silver Colloid Nanoparticles: Synthesis, Characterization, and Their Antibacterial Activity", J. Phys. Chem. B., vol. 110, No. 33, 2006, pp. 16248-16253.
Virender K. Sharma, et al., "Silver nanoparticles: Green synthesis and their antimicrobial activities", Advances in Colloid and Interface Science, vol. 145, 2009, pp. 83-96.
Iqbal M. Ismail, et al., "Mechanistic and kinetic study of the formation of silver nanoparticles by reduction of silver(I) in the presence of surfactants and macromolecules", Transition Metal Chemistry, vol. 40, No. 4, May 2015, pp. 371-378.

* cited by examiner

*Primary Examiner* — Tracy Vivlemore
*Assistant Examiner* — Monica A Shin
(74) *Attorney, Agent, or Firm* — Oblon, McClelland, Maier & Neustadt, L.L.P.

(57) ABSTRACT

A method of reducing silver(I) salts to silver nanoparticles employing a carbohydrate reductant in the presence of an inorganic base, a surfactant and optionally a polymer. The method is performed in an aqueous solution at a temperature up to 60° C. and for a duration of up to 40 minutes.

19 Claims, 10 Drawing Sheets

METHOD OF FORMING SILVER NANOPARTICLES AND A USE THEREOF

BACKGROUND OF THE INVENTION

Field of the Invention

This disclosure is directed to a method of reducing silver(I) salts to silver nanoparticles employing carbohydrate reductants. This disclosure is also directed to a method of preparing a colloid comprising the silver nanoparticles.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Silver nanoparticles have many applications in biotechnology, medicine, catalysis, microelectronics, cosmetics, adhesives, enhanced solar cells and biochemistry (Anil-Kumar S, Abyanesh M K, Gosavi S W, Kulkarni S K, Pasricha R, Ahmed M, Khan M I (2007) Biotechnol Lett 29:439; Schultz D A (2003) Curr Opin Biotech 14:13; Eigenheer R, Castellance E R, Nakamoto M Y, Gerner K T, Lampe A M, Wheeler K E (2014) Environ Sci NANO 1:238; Sharma V K, Yngard R A, Lin Y (2009) Adv Colloid Interface Sci 145:83; and Wigginton N S, de Titta A, Piccapietra F, Dobias J, Nesatyy V J, Suter M J F, Bernier-Latmani R (2010) Environ Sci Technol 44:2163, each incorporated herein by reference in their entirety). The silver nanoparticles can be formed and stabilized by chemical and physical methods. Chemical methods, such as electrochemical techniques, chemical reduction and photochemical reduction, are most widely used (Frattini A, Pellegri N, Nicastro D, de Sanctis O (2005) Mater Chem Phys 94:148, incorporated herein by reference in its entirety). Silver ions are reduced to silver atoms, followed by agglomeration of the atoms into oligomeric clusters (Kapoor S, Lawless D, Kennepohl P, Meisel D, Serpone N (1994) Langmuir 10:3018, incorporated herein by reference in its entirety). These clusters eventually form yellow colloidal silver nanoparticles in solution.

Karandikar et al. (European Patent No. EP2789235A1) discloses methods and compositions for antimicrobial silver compositions comprising silver nanoparticles, and methods for preparing silver nanoparticles with at least one stabilizing agent, one or more silver compounds, at least one reducing agent and a solvent. However, this reference employs reagents, such as polyacrylonitrile and diethyltoluamide (DEET), which are incompatible with biological systems.

In view of the foregoing, the objective of the present disclosure is to provide a method for producing biocompatible silver nanoparticles for applications such as biotechnology, medicine and cosmetics.

SUMMARY OF THE DISCLOSURE

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

A first aspect of the disclosure relates to a method of forming silver nanoparticles, comprising reacting a silver(I) salt with a carbohydrate reductant in an aqueous solution comprising: (i) the silver(I) salt, (ii) the carbohydrate reductant, (iii) water, (iv) an inorganic base, and (v) a surfactant, where the reacting is performed at a temperature up to 60° C. to form the silver nanoparticles.

In one embodiment, the reacting is performed for a period ranging from 1-40 minutes.

In another embodiment, the reacting is performed at a temperature ranging from 35-60° C.

In one embodiment, a concentration of the silver(I) salt in the aqueous solution ranges from 10-100 μM.

In another embodiment, the silver(I) salt is silver(I) nitrate.

In one embodiment, a concentration of the carbohydrate reductant in the aqueous solution ranges from more than 5 times to 800 times relative to the concentration of the silver(I) salt in the aqueous solution.

In another embodiment, the carbohydrate reductant is a polyhydroxy aldehyde.

In one embodiment, the carbohydrate reductant is at least one selected from the group consisting of glucose, lactose, galactose and ribose.

In another embodiment, the carbohydrate reductant is galactose.

In one embodiment, a concentration of the inorganic base in the aqueous solution ranges from more than 10 times to 620 times relative to the concentration of the silver(I) salt in the aqueous solution.

In another embodiment, the inorganic base is at least one of an alkali metal hydroxide and an alkali metal carbonate.

In a preferred embodiment, the inorganic base is sodium hydroxide.

In one embodiment, a concentration of the surfactant in the aqueous solution ranges from more than 10 times to 120 times relative to the concentration of the silver(I) salt in the aqueous solution.

In another embodiment, the surfactant is cetyltrimethylammonium bromide.

In one embodiment, the surfactant is sodium dodecyl sulfate.

In some embodiments, the aqueous solution further comprises a polymer, and a concentration of the polymer in the aqueous solution ranges from more than 0 ppm to 25 ppm.

In some embodiments, the polymer is chitosan and an average distance between the silver nanoparticles in the aqueous solution is in a range of 7-30 nm.

In one embodiment, the silver nanoparticles are of at least one shape selected from the group consisting of a sphere, a spheroid, and an ellipsoid.

In another embodiment, the silver nanoparticles have an average diameter of 10-50 nm.

A second aspect of the disclosure relates to a method of preparing a colloid, comprising reacting a silver(I) salt with a carbohydrate reductant in an aqueous solution comprising: (i) the silver(I) salt, (ii) the carbohydrate reductant, (iii) water, (iv) an inorganic base, (v) a surfactant, and (vi) optionally a polymer, isolating the silver nanoparticles, and suspending the silver nanoparticles in a solvent, where the reacting is performed at a temperature up to 60° C. to form the silver nanoparticles.

DETAILED DESCRIPTION OF THE DISCLOSURE

Figure 1:
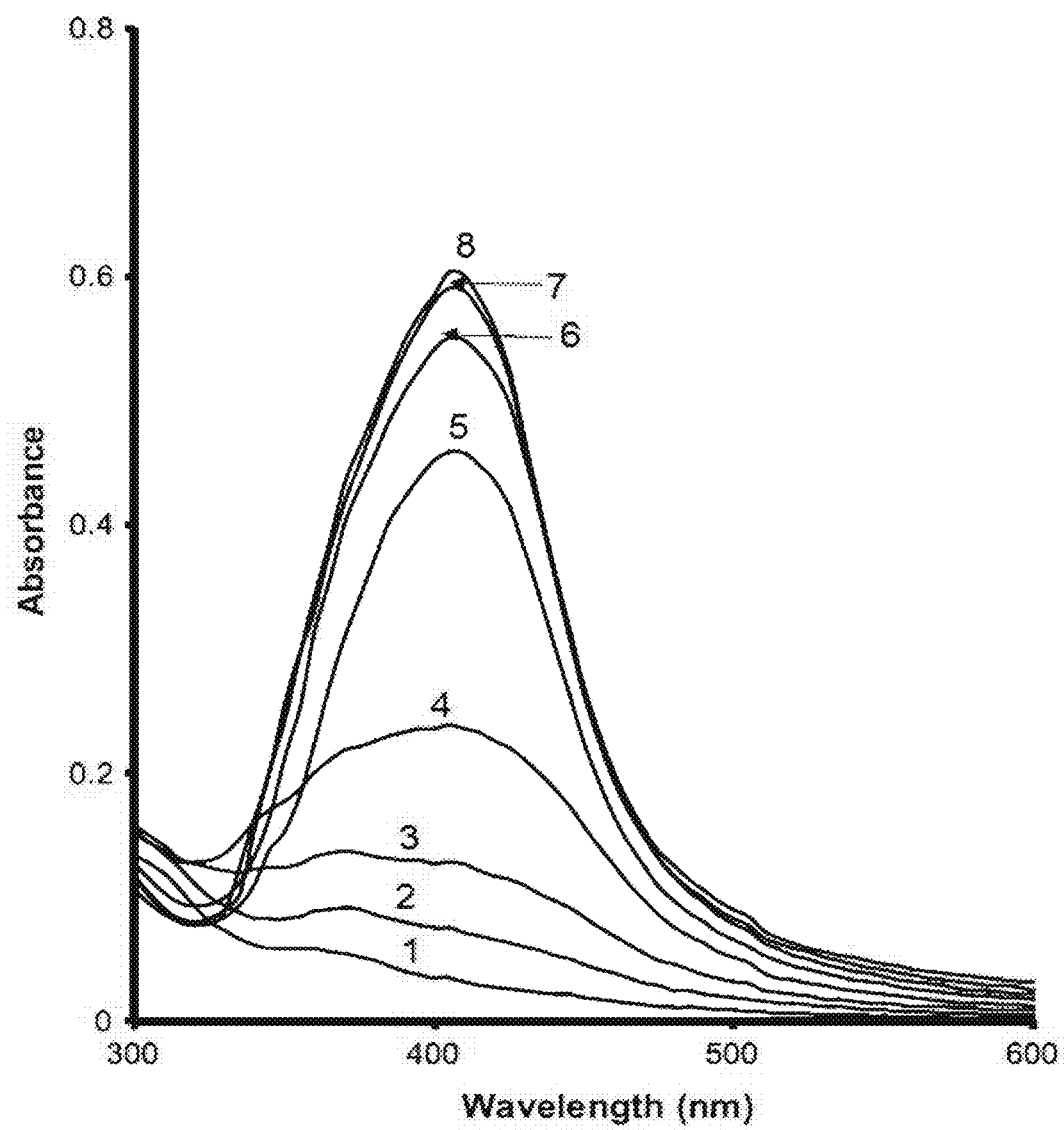
FIG. 1 is an overlay of the absorbance spectra of reaction mixtures recorded at 2 min (curve 1), 5 min (curve 2), 7 min (curve 3), 10 min (curve 4), 15 min (curve 5), 20 min (curve 6), 30 min (curve 7) and 40 min (curve 8) at $[Ag^+]=5.0\times10^{-5}$ mol dm$^{-3}$, [galactose]=$1.0\times10^{-2}$ mol dm$^{-3}$, [CTAB]=$1.0\times10^{-3}$ mol dm$^{-3}$, [OH$^-$]=$10.0\times10^{-3}$ mol dm$^{-3}$ and T=40.0° C.

Embodiments of the present disclosure will now be described more fully hereinafter with reference to the accompanying drawings, in which some, but not all embodiments of the disclosure are shown.

The first aspect of the disclosure relates to a method of forming silver nanoparticles, comprising reacting a silver(I) salt with a carbohydrate reductant in an aqueous solution comprising: (i) the silver(I) salt, (ii) the carbohydrate reductant, (iii) water, (iv) an inorganic base, and (v) a surfactant, where the reacting is performed at a temperature up to 60° C. to form the silver nanoparticles. The reacting may proceed for a period ranging from 1-40 minutes, preferably 15-40 minutes, more preferably 30-40 minutes. The aqueous solution may be heated to a temperature ranging from 35-60° C., preferably 40-55° C., more preferably 45-50° C. The aqueous solution may be stirred by employing a magnetic stirrer or an overhead stirrer. In another embodiment, the aqueous solution is left to stand (i.e. not stirred). An external heat source, such as a water bath or an oil bath, an oven, or a heating mantle, may be employed to heat the aqueous solution. In a preferred embodiment, the external heat source is a thermostatted thermocirculator. In one embodiment, the aqueous solution is not heated with microwave irradiation.

Prior to the heating step, the aforementioned reagents may be dissolved in water separately to form the respective solutions and then thermally equilibrated for 5-20 minutes, preferably 10-20 minutes, more preferably about 15-20 minutes in a thermostated water bath. After the reagents have achieved thermal equilibrium, they are mixed to form the aqueous solution. Preferably, the inorganic base solution and the surfactant solution are mixed with the silver(I) salt solution to form a first mixture and the galactose solution is mixed with the first mixture to initiate the formation of the silver nanoparticles.

Non-limiting examples of silver(I) salts include silver nitrate, silver acetate, silver sulfate, silver nitrite, silver salicylate, silver carbonate, silver phosphate, silver benzoate and silver halides such as silver fluoride, silver bromide, silver chloride and silver iodide. Most silver(I) salts are sparingly soluble or insoluble in water. Therefore, in a preferred embodiment, silver(I) nitrate is employed. A concentration of the silver(I) salt in the aqueous solution ranges from 10-100 μM, preferably 20-80 μM, more preferably 40-60 μM.

The carbohydrate reductant comprises a free aldehyde group which plays a key role in the reduction of silver(I) salts. Therefore, the carbohydrate reductant may be a polyhydroxy aldehyde such as glucose and/or galactose. In one embodiment, the carbohydrate reductant is a monosaccharide such as galactose. In another embodiment, the carbohydrate reductant is a disaccharide such as cellobiose, lactose, gentiobiose, isomaltose, mannobiose, xylobiose, laminaribiose and maltose. The carbohydrate reductant may also be a polyhydroxy ketone, such as fructose, sorbose and tagatose, or a mixture thereof, which comprises a ketone functional group that tautomerizes in a solution to form a free aldehyde group. Preferably, the carbohydrate reductant is glucose, lactose, galactose, ribose or a mixture thereof. More preferably, the carbohydrate reductant is galactose because it is compatible with surfactants and is a stronger reducing agent than glucose (Blackburn R S, Harvey A (2004) Environ Sci Technol 38:4034; and Ismail I M, Ewais H A (2015) Transition Met Chem 40:371, each incorporated herein by reference in its entirety). A concentration of the carbohydrate reductant in the aqueous solution ranges from 0.05-80 mM, preferably 1-80 mM, more preferably 2-32 mM, and even more preferably 8-24 mM. The concentration of the carbohydrate reductant in the aqueous solution ranges from more than 5 times to 800 times, preferably 66-800 times, more preferably 100-400 times, and even more preferably 200-400 times relative to the concentration of the silver(I) salt in the aqueous solution.

The carbohydrate reductant may be added in several batches or, preferably, all at once. In one embodiment, the carbohydrate reductant is added in three batches with an interval of about two minutes between each addition. The carbohydrate reductant may be thermally equilibrated by the aforementioned method and then added to the first mixture. In one embodiment, the carbohydrate reductant is not thermally equilibrated before adding to the first mixture.

An inorganic base catalyzes the formation of silver nanoparticles by abstracting the α-proton of the aforementioned carbohydrate reductants, causing the ring to open and forming the aldehyde functional group which readily reduces silver(I) to elemental silver. The inorganic base may be an alkali metal hydroxide, such as sodium hydroxide, potassium hydroxide and lithium hydroxide, an alkali metal carbonate, such as potassium carbonate, sodium carbonate and caesium carbonate, or a mixture thereof. Preferably, the inorganic base is sodium hydroxide. A concentration of the inorganic base in the aqueous solution ranges from 0.1-62 mM, preferably 0.3-58 mM, more preferably 4-50 mM, and even more preferably 16-32 mM. The concentration of the inorganic base in the aqueous solution ranges from more than 10 times to 620 times, preferably 30-580 times, more preferably 200-620 times, and even more preferably 400-520 times relative to the concentration of the silver(I) salt in the aqueous solution.

A surfactant governs the shape and size of the nanoparticles. The use of surfactants and polymers may be important to obtain stable monodisperse nanoparticles (Heinzman S W, Gamen B (1982) J Am Chem Soc 104:6801, incorporated herein by reference in its entirety). The surfactants and polymers form micelles, which increase the rate of bimolecular reactions by concentrating the silver(I) ion and the carbohydrate reductant at the surfaces of micelles. Electrostatic and medium effects are responsible for the incorporation of reactants into or onto a micelle.

Anionic surfactants, such as sodium stearate and sodium dodecylsulfate, or cationic surfactants, such as cetyltrimethylammonium bromide and cetylpyridinium chloride, may prevent agglomeration of the formed silver nanoparticles. A concentration of the surfactant in the aqueous solution ranges from 0.1-12 mM, preferably 0.4-8 mM, more preferably 0.8-3 mM. The concentration of the surfactant in the aqueous solution ranges from more than 10 times to 120 times, preferably 20-100 times, more preferably 20-50 times relative to the concentration of the silver(I) salt in the aqueous solution.

The surfactant may be cetyltrimethylammonium bromide, and a concentration of cetyltrimethylammonium bromide in the aqueous solution ranges from 0.1-8 mM, preferably 0.2-3.2 mM, more preferably 0.4-1.2 mM. The concentration of the cetyltrimethylammonium bromide ranges from more than 10 times to 80 times, preferably 10-40 times, more preferably 10-20 times relative to the concentration of the silver(I) salt in the aqueous solution.

In a preferred embodiment, the surfactant is sodium dodecyl sulfate, and a concentration of sodium dodecyl sulfate in the aqueous solution ranges from 0.1-10 mM, preferably 1-8 mM, more preferably 3.2-6 mM. The concentration of sodium dodecyl sulfate in the aqueous solution ranges from more than 10 times to 100 times, preferably 50-100 times, more preferably 80-100 times relative to the concentration of the silver(I) salt in the aqueous solution.

In some embodiments, the aqueous solution comprises a polymer. A concentration of the polymer in the aqueous solution ranges from more than 0 ppm to 25 ppm, preferably 5-20 ppm, more preferably 5-15 ppm.

Polymers, such as Triton X-100, polyphosphate, polyacrylate, poly(vinyl alcohol) and poly(ethylamine), may be added in small amounts to stabilize the growing silver nanoparticles. Preferably, natural polymers and biomolecules may be added in the preparation of silver nanoparticles because they are non-toxic and biocompatible. An association between ionic micelles and polymers usually stabilizes the micelles and thus reduces the critical micelle concentration. As used herein, critical micelle concentration refers to the concentration of surfactants above which micelles form. The surfactant-polymer interaction depends on both the relative charge and hydrophobicity of the surfactant-polymer pair.

In a preferred embodiment, the polymer is chitosan. Derivatives of chitosan, such as chitosan oligosaccharide lactate and glycol chitosan, which have a higher solubility in water than the unmodified chitosan may also be used. Chitosan is a polysaccharide copolymer of N-acetyl-D-glucosamine and D-glucosamine, obtained by the alkaline deacetylation of chitin obtained from crustaceans, such as shrimps, squids and crabs (Onishi H, Machida Y (1999) Biomaterials 20:175; Yanga J, Shibb I, Tzengc Y, Wang S (2000) Enzyme Microb Technol 26:406; and Khan T A, Peh K K, Chng H S (2002) J Pharm Sci 5:205, each incorporated herein by reference in their entirety). Chitosan has been used as a non-toxic, biodegradable, biocompatible and environmental-friendly material with many superior properties (Jigar M J, Sinha V K (2007) Carbohydr Polym 67:427, incorporated herein by reference in its entirety). Chitosan has many industrial applications in areas such as wastewater treatment, medicine, food and cosmetics (Cho Y W, Cho Y N, Chung S H, Ko W (1999) Biomaterials 20:2139; 8. Khor E, Lim L Y (2003) Biomaterials 24:2339; and Crini G (2006) Bioresour Technol 97:1061, each incorporated herein by reference in their entirety). It is also being studied for food packaging films, bone substitutes, artificial skin, biomedical applications and pH-sensitive drug delivery (Jayakumar R, Menon D, Manzoor K, Nair S V (2010) Carbohydr Polym 82:227, incorporated herein by reference in its entirety).

The chitosan employed in this disclosure may have a weight average molecular weight ranging from 100-400 kDa, preferably 100-300 kDa, more preferably 100-200 kDa. The weight average molecular weight may be measured by gel permeation chromatography. A degree of deacetylation of chitosan ranges from more than 40 wt %, preferably more than 60 wt %, more preferably more than 75 wt % relative to the total weight of chitosan. As used herein, the term "degree of deacetylation" refers to the percentage mass of D-glucosamine present in chitosan and can be determined by methods, such as titration and UV-vis spectrometry, which are known to those skilled in the art (Yuan et al. (2011) Materials 4:1399, incorporated herein by reference in its entirety).

The method produces silver nanoparticles with a shape that may be a sphere, a spheroid, an ellipsoid or a polygon etc. The silver nanoparticles may also have an irregular shape. In a preferred embodiment, the silver nanoparticles are a mixture of spheroids and ellipsoids. The silver nanoparticles may be monodisperse, or preferably, polydisperse. The silver nanoparticles have an average diameter of 10-50 nm, preferably 15-45 nm, more preferably 20-40 nm. For particles with a polygonal shape, the term "diameter", as used herein, refers to the greatest possible distance measured from a vertex of a polygon through the center of the face to the vertex on the opposite side. For spheres, spheroids, ellipsoids and irregular-shaped particles, "diameter" refers to the greatest possible distance measured from one point on the particle through the center of the particle to a point directly across from it. In the absence of the polymer, the silver nanoparticles may cluster and form agglomerates with a size ranging from 200-5,000 nm, preferably 300-4,000 nm, more preferably 300-3,000 nm. In the presence of a polymer, preferably chitosan, the silver nanoparticles are separated from one another and do not form agglomerates. A distance between the nanoparticles is measured from an outer surface of a first nanoparticle to an outer surface of a second nanoparticle located closest to the first nanoparticle. An average distance ranges from 7-30 nm, preferably 7-20 nm, more preferably 7-15 nm.

The formation of silver nanoparticles in aqueous solutions proceeds via several different species of silver metal particles. Species, such as $Ag_2^+$, $Ag_4^{2+}$, $Ag_3^{2+}$, $Ag_6^{4+}$, and $Ag_9^+$, exist in aqueous medium. Preferably, $Ag_4^{2+}$ is the dominant species because it is relatively more stable than the other polyatomic silver species and the stability of $Ag_4^{2+}$ may be improved in the presence of surfactants.

The second aspect of the disclosure relates to a colloid comprising the silver nanoparticles which are dispersed in a solvent. The formed silver nanoparticles may be isolated from the unreacted reagents by centrifugation at 3000 to 5000 rpm, for example, for 5-15 minutes, preferably 10 minutes. The nanoparticles may also be filtered with a membrane. The nanoparticles may be washed several times and suspended in a solvent or carrier of interest. Non-limiting examples of solvent and/or carrier include organic solvents, such as methanol, dimethyl sulfoxide, tetrahydrofuran, and aqueous solutions such as phosphate-buffered saline and water.

The colloid is prepared by mixing the nanoparticles with the solvent to a concentration range of 1-50 mg nanoparticles per ml of colloid, preferably 1-25 mg/ml, more preferably 1-10 mg/ml. The colloid may be sonicated to ensure a homogeneous suspension of the nanoparticles in the solvent. The colloid may be colloidally stable at ambient conditions for at least 1 month, preferably at least 4 months, more preferably at least 11 months. The term "colloidally stable", as used herein, means that the nanoparticles do not agglomerate at a measureable rate nor precipitate from solution. For example, there is substantially no precipitation and/or change in the size of the nanoparticles over the course of several months. Silver nanoparticles have many applications in biotechnology, medicine, catalysis, microelectronics, cosmetics, adhesives, enhanced solar cells and biochemistry (Anil-Kumar S, Abyanesh M K, Gosavi S W, Kulkarni S K, Pasricha R, Ahmed M, Khan M I (2007) Biotechnol Lett 29:439; Schultz D A (2003) Curr Opin Biotech 14:13; Eigenheer R, Castellance E R, Nakamoto M Y, Gerner K T, Lampe A M, Wheeler K E (2014) Environ Sci NANO 1:238; Sharma V K, Yngard R A, Lin Y (2009) Adv Colloid Interface Sci 145:83; and Wigginton N S, de Titta A, Piccapietra F, Dobias J, Nesatyy V J, Suter M J F, Bernier-Latmani R (2010) Environ Sci Technol 44:2163, each incorporated herein by reference in their entirety). For example, the antibacterial activity of the colloid may be tested by contacting an aqueous colloid with bacteria colonies in antibacterial activity assays. Non-limiting examples of bacteria used may be *Escherichia coli* (*E. coli*), *Staphylococcus aureus* (*S. aureus*), and *Bacillus subtilis* (*B. subtilis*).

Having generally described this disclosure, a further understanding can be obtained by reference to certain specific examples which are provided herein for purposes of illustration only and are not intended to be limiting unless otherwise specified.

Example 1 Reagents and Experimental Methods

Galactoses, sodium hydroxide, silver nitrate, chitosan, acetic acid, cetyltrimethylammonium bromide and sodium dodecyl sulfate (Fluka and BDH) were used without further purification. The solutions of silver nitrate and galactose were prepared daily to avoid aerial oxidation. Doubly distilled water was used for the preparation of all solutions. Chitosan (1.0%) solution was prepared by dissolving chitosan (1.0 g) in acetic acid (100 ml, 1.0 M).

A UV-visible LABOMED, INC UVD-2960 spectrophotometer and PerkinElmer EZ-150 spectrophotometer were used to monitor the absorbance of the silver nanoparticles while they were formed. A transmission electron microscope (JEOL, JEM-1011, Japan) was used to determine and record the size of the silver nanoparticles. The preparation of samples was carried out by placing a drop of working solution on a carbon-coated standard copper grid (300 mesh) operating at 80 kV. The particles were imaged by LEO 440i scanning electron microscopy (SEM) at an accelerating voltage of 20 kV.

The ultraviolet-visible absorption spectra of the silver nanoparticles were recorded for a period of time using a LABOMED and INC UVD-2960 spectrophotometer. All reactants were thermally equilibrated for about 20 min in an automatic circulation thermostat, thoroughly mixed and quickly transferred to an absorption cell. The reaction rates were measured by monitoring the absorbance of the silver nanoparticles at 410 nm (where the absorbance of the nanoparticles is maximal), using a PerkinElmer EZ-150 spectrophotometer. The thermostat was provided with a special pumping system for circulating water at regulated temperature in the cell holder.

Pseudo first-order conditions were maintained in all runs by the presence of a large excess of galactose (more than ten-fold). Pseudo first-order rate constants $k_{obs}$ were obtained from the slopes of plots of ln a/(1−a) versus time with a fixed-time method, where a=$A_t/A_\infty$ and $A_t$ and $A_\infty$ are the absorbance values at times t and infinity, respectively (Esumi K, Hosoyo T, Yamahira A, Torigoe K (2000) J Colloid Interface Sci 226:346, incorporated herein by reference in its entirety).

The preparation of silver nanoparticles by the reduction of silver nitrate solution with galactose in the presence of micelles in aqueous medium was investigated. A series of runs was carried out using different concentrations of reductant, silver(I) ions and cetyltrimethylammonium bromide to obtain a transparent yellow colloid comprising silver nanoparticles. For example, 2.0 ml of a 0.001 mol dm$^{-3}$ solution of silver nitrate and 4.0 ml of a 0.1 mol dm$^{-3}$ sodium hydroxide solution were mixed with 4.0 ml of a 0.01 mol dm$^{-3}$ cetyltrimethylammonium bromide solution. A 2.0 ml portion of a 0.2 mol dm$^{-3}$ solution of galactose was added to initiate the reaction, such that the total volume of the reaction mixture was always 40 ml. The presence of a pale yellow color indicated the formation of silver nanoparticles (Henglein A (1993) J Phys Chem 97:5457, incorporated herein by reference in its entirety).

Figure 2:
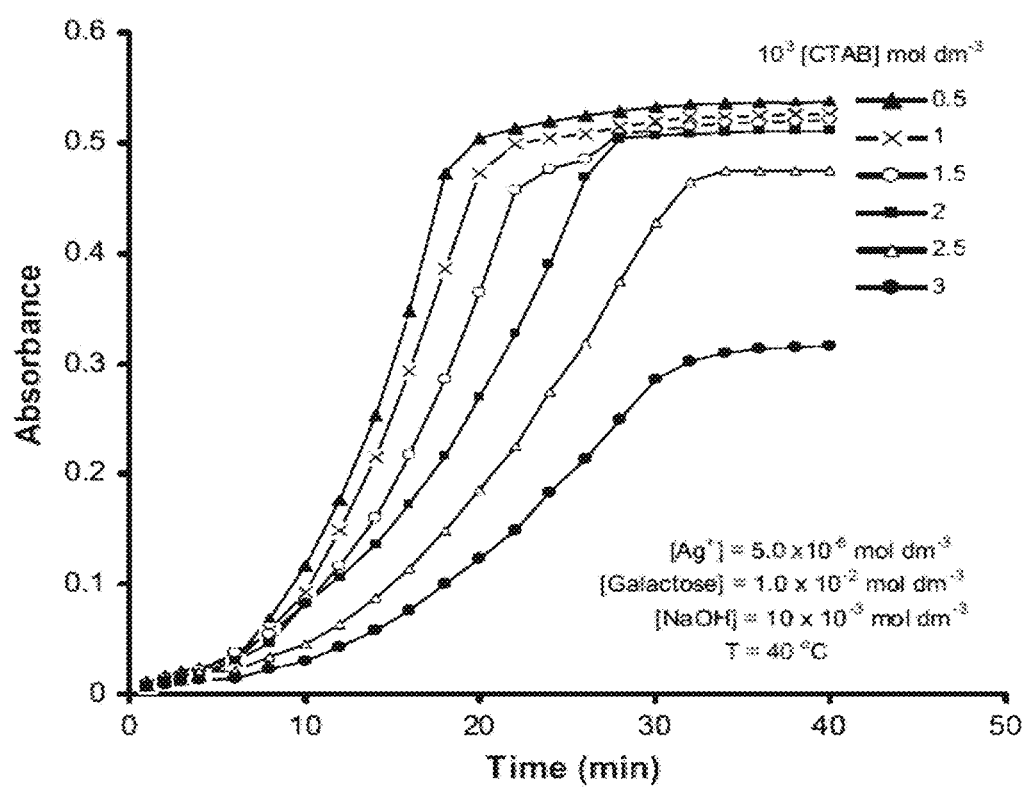
FIG. 2 is an overlay of the absorbance values at 410 nm recorded at different time points for reactions performed with different concentrations of cetyltrimethylammonium bromide, CTAB.

Example 2 the Effects of Cetyltrimethylammonium Bromide (CTAB) and Sodium Dodecyl Sulfate (SDS) on the Formation of Silver Nanoparticles The UV-Vis absorption spectra (FIG. 1) indicate the silver nanoparticles absorb strongly at 410 nm, leading to an appearance of a yellow solution. The absorption plasmon band at 410 nm is characteristic of spherical or roughly spherical silver nanoparticles. The effects of surfactants were studied at [Ag$^+$]=5.0×10$^{-5}$ mol dm$^{-3}$, [galactose]=1.0× 10$^{-2}$ mol dm$^{-3}$, [OH$^-$]=10×10$^{-3}$ mol dm$^{-3}$, [CTAB]= [SDS]=0.5 mmol dm$^{-3}$ to 4.0 mmol dm$^{-3}$ and T=40.0° C. The results are summarized in Table 1 and shown in FIG. 2. The reaction rate decreases as [CTAB] increases but increases with increasing [SDS] up to 2.5×10$^{-3}$ mol dm$^{-3}$ (Table 1). The observations can be explained by incorporation/solubilization of Ag$^+$/galactose in the Stern layer of sodium dodecyl sulfate, which agrees with previous observations (Kabir-ud-Din A, Morshed A M, Khan Z (2002) Carbohydr Res 337:1573, incorporated herein by reference in its entirety). At higher [SDS]=2.5×10$^{-3}$ mol dm$^{-3}$, the reaction mixtures became turbid and a transparent silver sol was not formed.

Micelles catalyze reactions by solubilizing and/or incorporating reactants into the small volume of micelles through electrostatic, hydrophobic, hydrogen bonding and van der Waals forces (Bunton C A, Savelli G (1986) Adv Phys Org Chem 22:213; and Bunton C A (1997) J Mol Liq 72:231, each incorporated herein by reference in their entirety). The different reaction rates observed in the presence of sodium dodecyl sulfate or cetyltrimethylammonium bromide micelles can be explained by the interactions between the micelles and the silver(I) ion, Ag$^+$. The formation of an ion pair (—OSO$_3^-$Ag$^+$) with the terminal negative functional group of sodium dodecyl sulfate micelles may concentrate $Ag^+$ in the reaction site (i.e., the Stern layer, as most ionic micelle-mediated reactions are believed to occur in this region). Electrostatic repulsion between the terminal positive functional group ($-N^+(CH_3)_3$) of cetyltrimethylammonium bromide micelles and $Ag^+$ ions may retard the formation of silver nanoparticles,

TABLE 1

The effect of micelles in the formation of silver nanoparticles at $[Ag^+] = 5.0 \times 10^{-5}$ mol $dm^{-3}$, [galactose] = $1.0 \times 10^{-2}$ mol $dm^{-3}$, [NaOH] = $10.0 \times 10^{-3}$ mol $dm^{-3}$ and T = 40.0° C.

| $10^3$ [Micelles] (mol $dm^{-3}$) | $10^3$ $k_{obs}$ (CTAB) ($s^{-1}$) | $10^3$ $k_{obs}$ (SDS) ($s^{-1}$) |
| --- | --- | --- |
| 0.50 | 3.76 | 2.85 |
| 1.00 | 3.23 | 3.48 |
| 1.50 | 2.83 | 3.89 |
| 2.00 | 2.26 | 4.35 |
| 2.50 | 1.64 | 4.59 |
| 3.00 | 1.03 | Turbid |
| 4.00 | — | Turbid |

Figure 3:
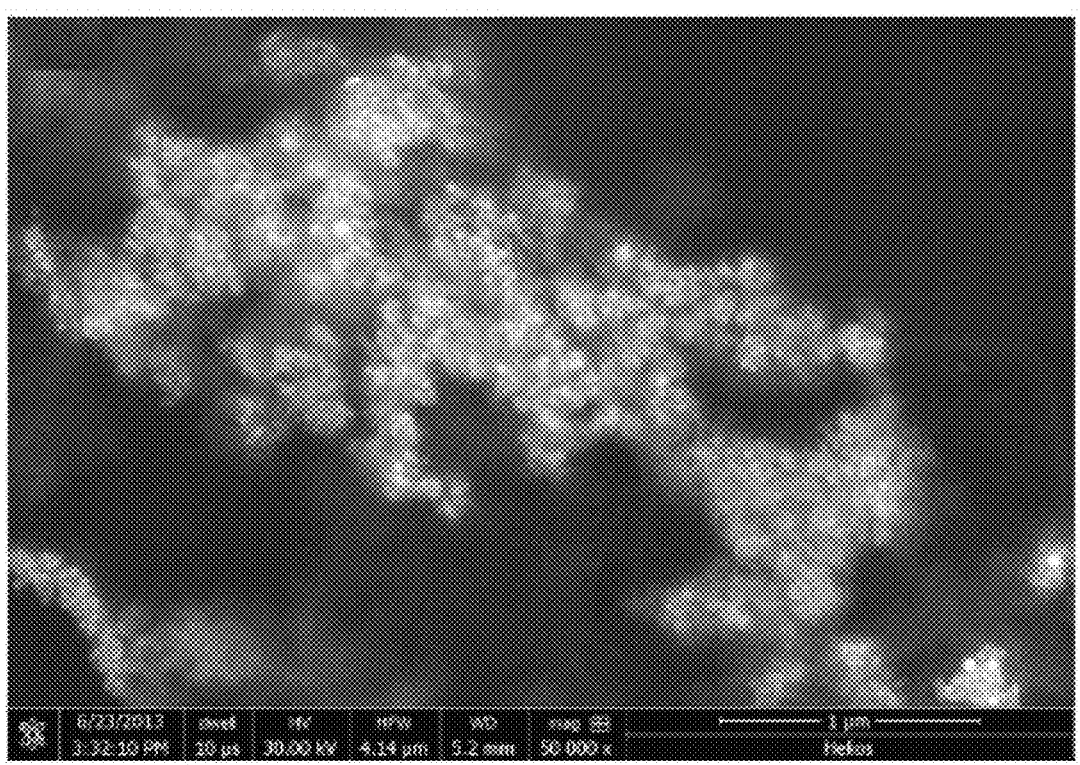
FIG. 3 is a scanning electron micrograph of silver nanoparticles that were obtained under the experimental conditions employed for the embodiment shown by FIG. 1.
Figure 4:
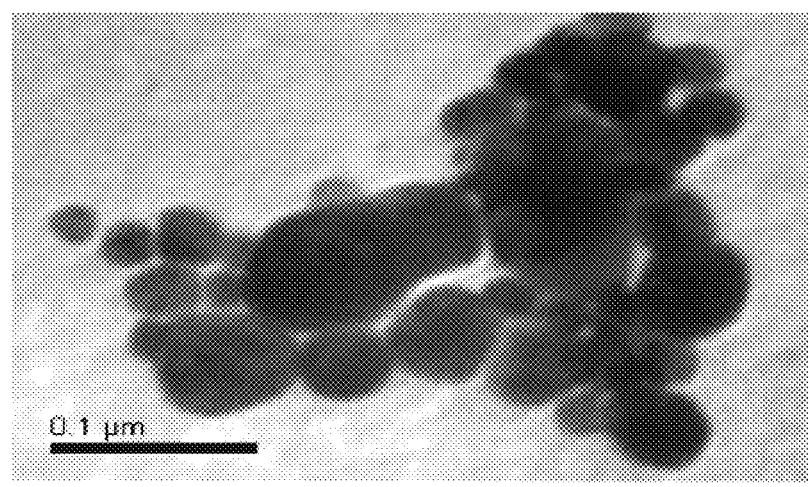
FIG. 4 is a transmission electron micrograph of silver nanoparticles that were obtained under the experimental conditions employed for the embodiment shown by FIG. 1.

A SEM image of the prepared silver nanoparticles is shown in FIG. 3. The particles range in size from 14.6 nm to 27.8 nm and have various shapes, including spherical and irregular, with some aggregation. FIG. 4 shows a TEM image of the nanoparticles with an average diameter ranging from 15.3-40 nm. The TEM image confirms that the cetyltrimethylammonium bromide stabilized particles are spherical rather than hexagonal forms of silver nanocrystals, as was observed for the reduction of $Ag^+$ with hydrazine (Tan Y, Li Y, Zhu D (2003) J Colloid Interface Sci 258:244, incorporated herein by reference in its entirety).

Example 3 the Role of Chitosan in Formation of Nanoparticles

Figure 5:
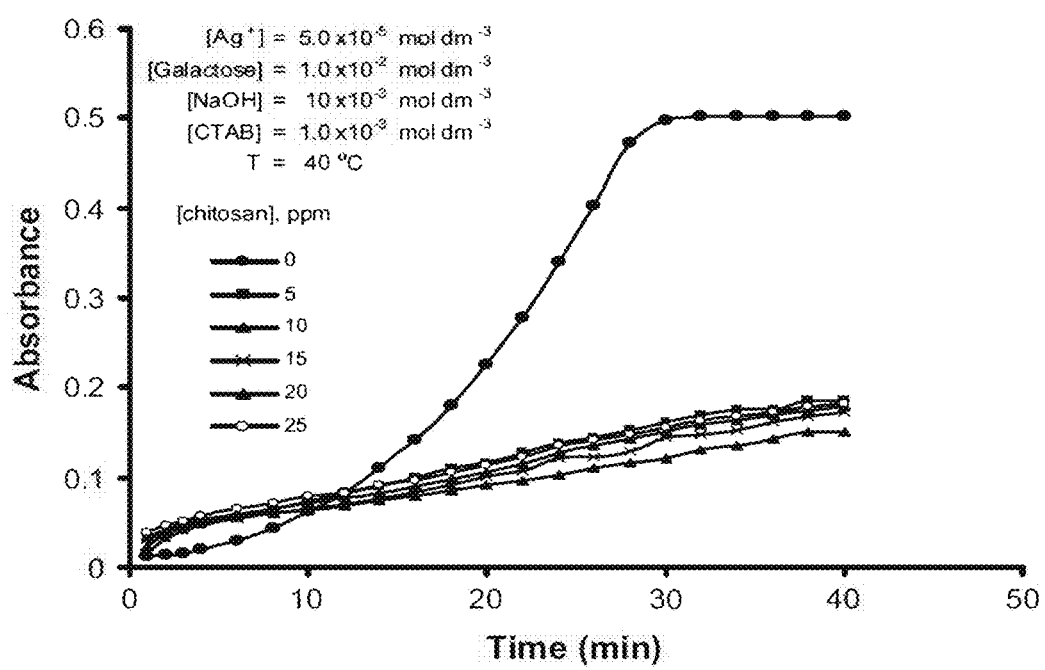
FIG. 5 is an overlay of the absorbance values at 410 nm recorded at different time points for reactions performed with different concentrations of chitosan.
Figure 6:
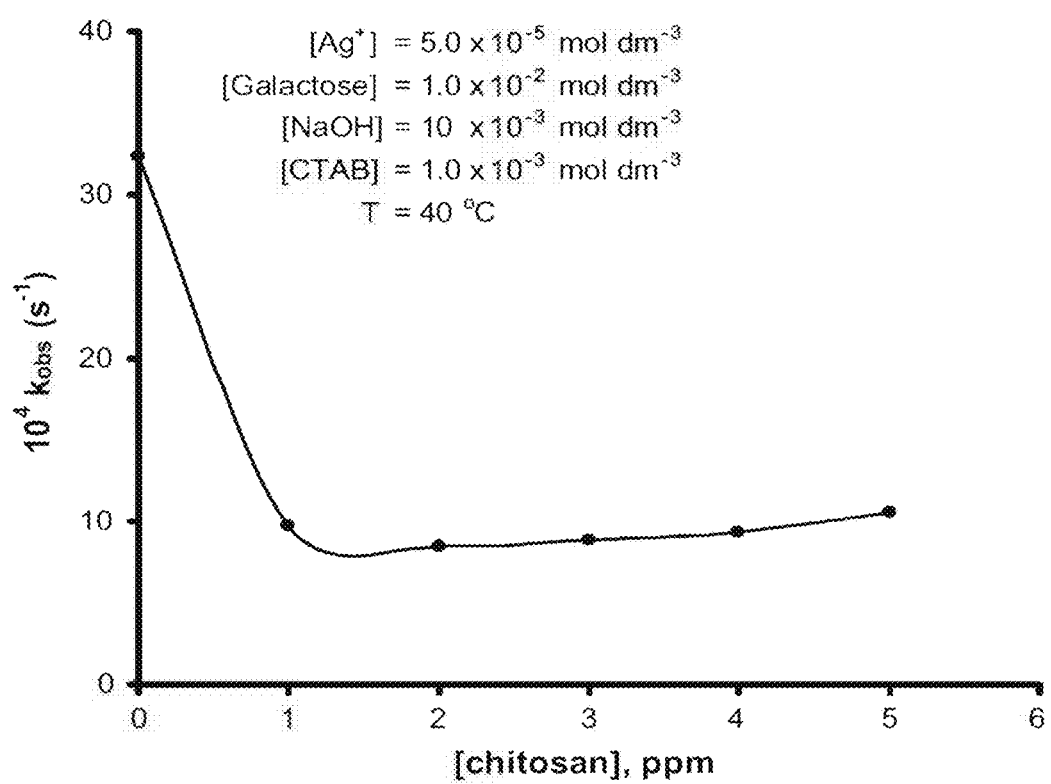
FIG. 6 is a plot showing the effect of the concentration of chitosan on the pseudo first-order rate constants for formation of silver nanoparticles.

The effect of chitosan on the present system was investigated at $[Ag^+]=5.0\times10^{-5}$ mol $dm^{-3}$, [galactose]=$1.0\times10^{-2}$ mol $dm^{-3}$, [NaOH]=$10.0\times10^{-3}$ mol $dm^{-3}$, [CTAB]=$10^{-3}$ mol $dm^{-3}$ and T=40° C. for a concentration of chitosan ranging from 5.0-25 ppm. To analyze the kinetics of the particle formation, absorbance values measured at 410 nm were plotted against time for experiments that included and excluded chitosan (FIG. 5). The decrease in absorbance of the silver sols in the presence of chitosan may be explained by the adsorption of chitosan onto the surfaces of the silver nanoparticles, increasing their Fermi level. On the other hand, a decrease in the reactant concentration at the reaction site could not be ruled out completely in the presence of chitosan. FIG. 6 shows that the reaction is inhibited in the presence of chitosan. A noticeable inhibition effect (about 70% inhibition) was observed at low concentrations of chitosan. Thus, it may be possible that the solubilization/incorporation of the reactants into the cetyltrimethylammonium bromide micelles was diminished but not totally prevented by the presence of chitosan at the micelle surface (Wang W, Wang J, Sun P, Yuan Z, Ding D, Chen T (2008) Mater Lett 62:711, incorporated herein by reference in its entirety). Since chitosan is more hydrophobic than galactose, it have greater affinity for the micelles. The chitosan may be located in the Stern layer.

Figure 7:
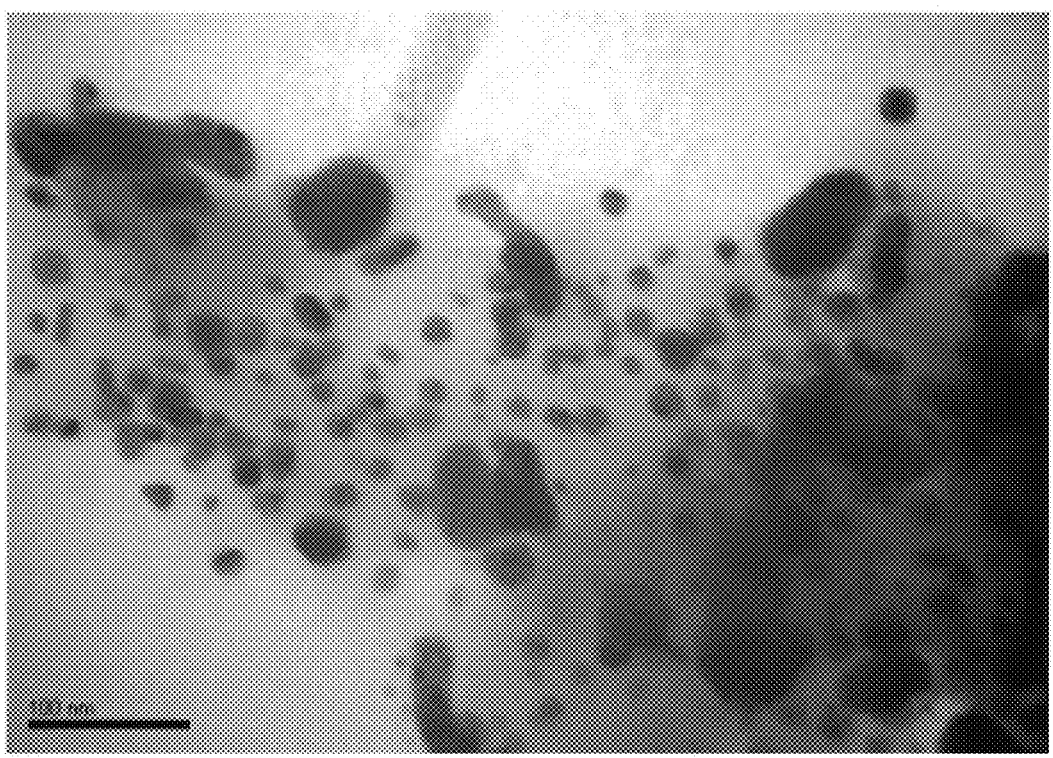
FIG. 7 is a transmission electron micrograph of silver nanoparticles that were obtained under the experimental conditions employed for the embodiment shown by FIG. 6.

A TEM image (FIG. 7) of the silver nanoparticles obtained in the presence of chitosan do not aggregate. However, the silver nanoparticles are spherical and of different particle sizes (i.e. polydisperse). These findings also suggest that the molecules of chitosan are strongly adsorbed on the surface of the particles suppressing particle aggregation. The presence of chitosan may decrease the nucleation rate, and hence, the bulk of the particles have a smaller diameter (about 11 nm). Comparison of spectroscopic, kinetic and TEM data clearly indicates that the shape, size distribution, nature of reaction-time curves, mechanism, aggregation, cross-linking and polydispersity, except the rate and size of silver nanoparticles formation, all follow the same pattern in the absence and presence of chitosan.

Example 4 the Formation of Nanoparticles in Alkaline Medium

Figure 8:
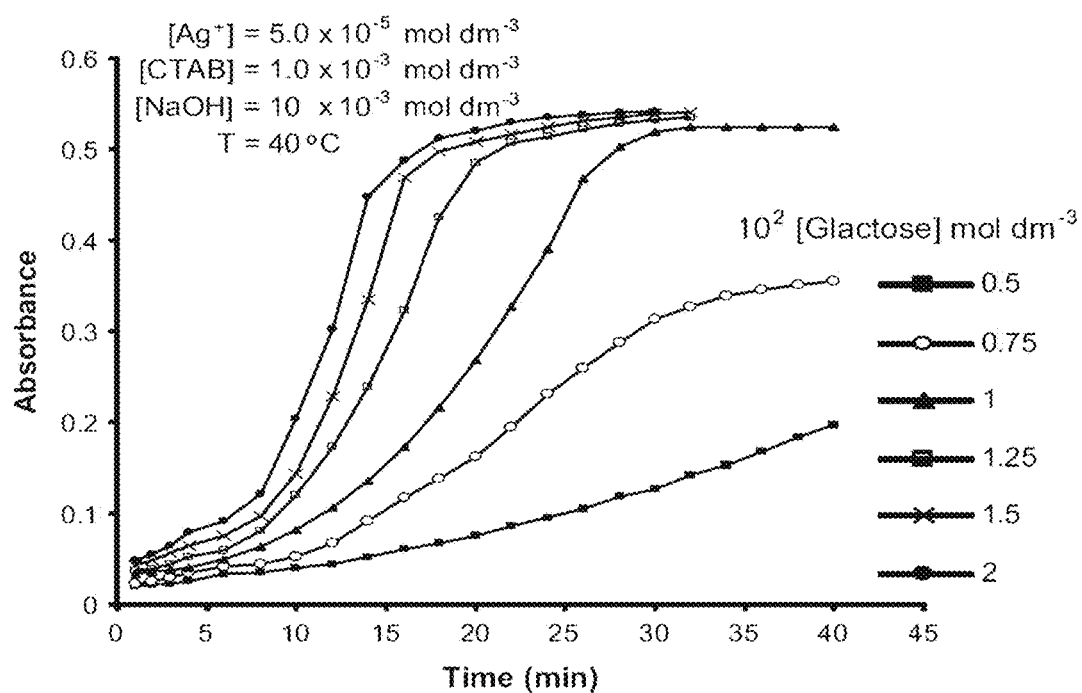
FIG. 8 is an overlay of the absorbance values at 410 nm recorded at different time points for reactions performed with different concentrations of galactose.
Figure 9:
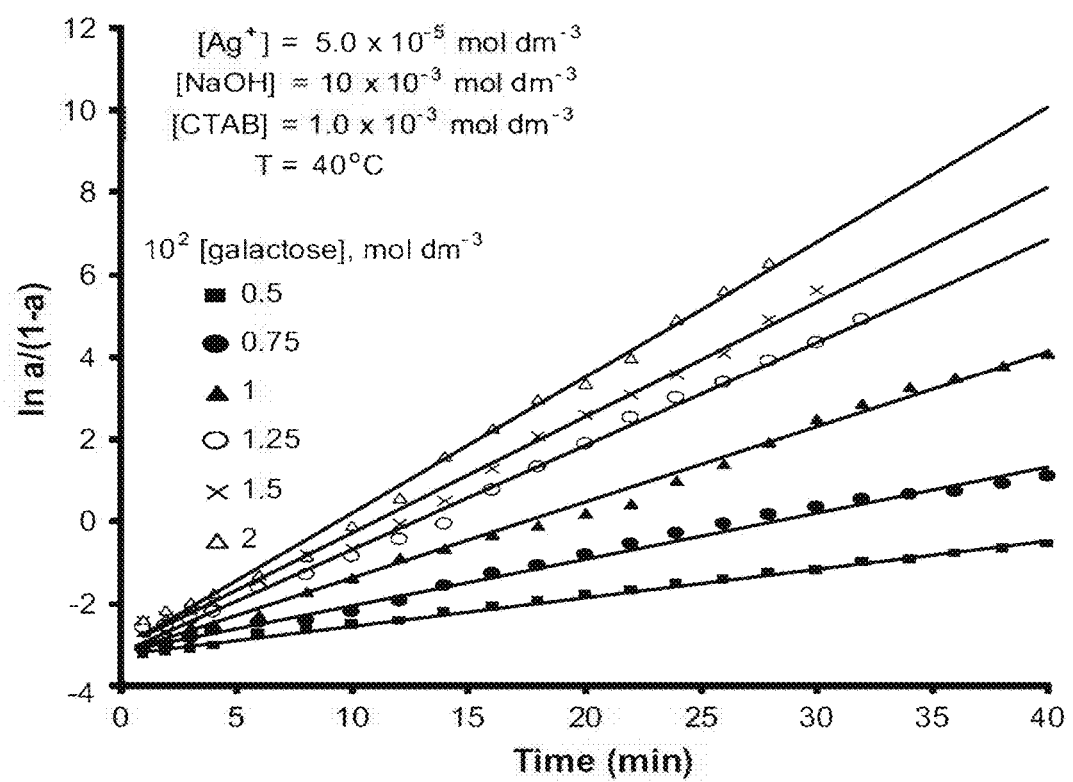
FIG. 9 is a plot of ln a/(1−a) versus time at different concentrations of galactose.

The system was studied at different concentrations of $Ag^+$, galactose, NaOH and cetyltrimethylammonium bromide over a temperature range of 35-50° C. Plots of absorbance versus time (FIG. 8) showed autocatalytic behavior in the silver sol formation. This observation can be attributed to the formation of metal nucleation centers catalyzes the reduction of other silver ions present in solution. Plots of ln a/(1−a) against time are linear (FIG. 9). The values of the rate constants were obtained from the slopes of plots of ln a/(1−a) versus time (Table 2). The constant values of $k_{obs}$ over a range of silver(I) ion concentration (25 μmol $dm^{-3}$ to 75 μmol $dm^{-3}$ at fixed galactose concentration indicates first-order dependence on $[Ag^+]$ (Table 2). This is represented by Eq. (1).

$$\text{Rate} = k_{obs}[Ag^+] \tag{1}$$

The dependence of the observed rate constant, $k_{obs}$, on galactose (R—CHO) was studied over the concentration range, 5 mmol $dm^{-3}$ to 20 mmol$^{-3}$, at fixed $[Ag^+]=5.0\times10^{-5}$ mol $dm^{-3}$, [NaOH]=$10\times10^{-3}$ mol $dm^{-3}$ and [CTAB]=$1.0\times10^{-3}$ mol $dm^{-3}$ at T=40° C. A plot of $k_{obs}$ versus [R—CHO] was linear without an intercept, obeying the linear equation: y=mx with a correlation coefficient of R=0.9986. This can be described by Eq. (2):

$$k_{obs} = k_1[\text{R—CHO}] \tag{2}$$

Figure 10:
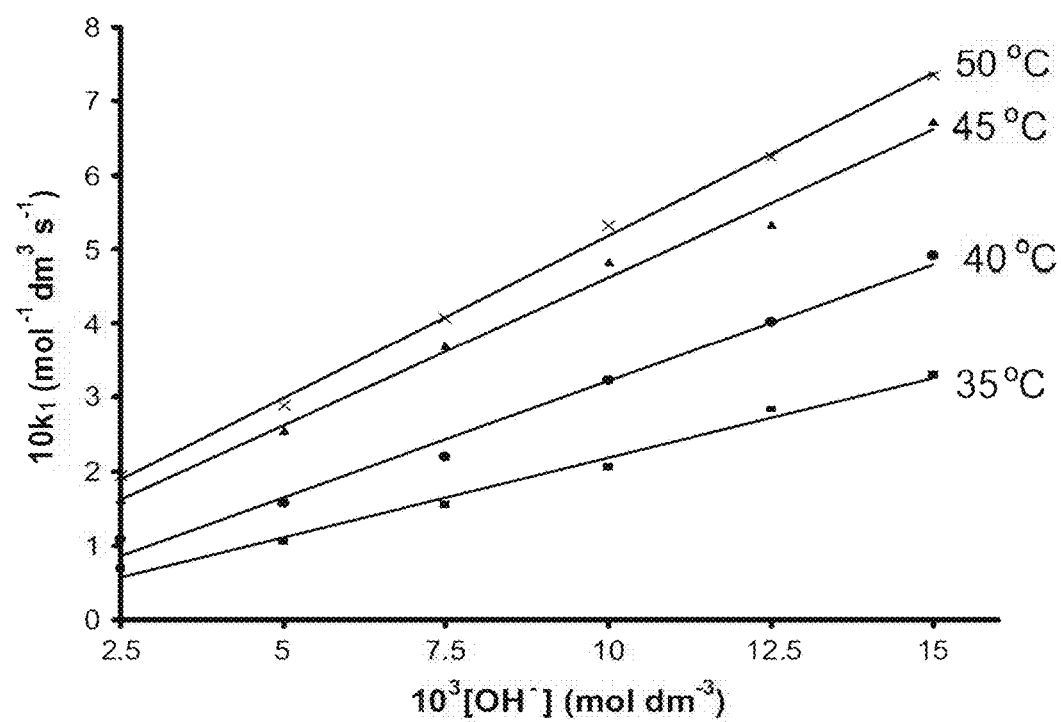
FIG. 10 is a plot of a first rate constant, $k_1$, versus the concentration of hydroxide ions at different temperatures.

The kinetics was studied over hydroxide ion concentration ranging from 2.5 mmol $dm^{-3}$ to 15.0 mmol $dm^{-3}$ at different temperatures. The values of $k_1$ with [NaOH] at different temperatures are represented in Table 3 and show that the rate increased gradually with increasing [NaOH]. Plots of $k_1$ against [OH$^-$] were linear with intercepts (FIG. 10). These observations can be described by Eq. (3).

$$k_1 = k_2 + k_3[\text{OH}^-] \tag{3}$$

From Eqs. (1), (2) and (3), the rate law for the reduction of silver(I) ions by galactose is given by Eq. (4).

$$\text{Rate} = (k_2 + k_3[\text{OH}^-])[Ag^+][\text{R—CHO}] \tag{4}$$

and $$k_{obs} = [\text{R—CHO}](k_2 + k_3[\text{OH}^-]) \tag{5}$$

The values $k_2$ and $k_3$ are collected in Table 4, as obtained from the intercepts and the slopes, respectively, of FIG. 10. The enthalpies of activation $\Delta H_2^*$ and $\Delta H_3^*$ related to $k_2$ and $k_3$ were calculated from a least squares fit to the transition state theory equation to be 187 kJ $mol^{-1}$ and 37.5 kJ $mol^{-1}$, respectively. The corresponding entropies of activation $\Delta S_2^*$ and $\Delta S_3^*$ were calculated to be −315 $JK^{-1}$ $mol^{-1}$ and −97.6 $JK^{-1}$ $mol^{-1}$, respectively.

The formation of silver sol in aqueous medium proceeds via several different species of silver metal particles. Species including $Ag_2^+$, $Ag_4^{2+}$, $Ag_3^{2+}$, $Ag_6^{4+}$, and $Ag_9^+$ exist in aqueous medium. Of these, $Ag_4^{2+}$ is the more stable species in the presence of surfactants. Sodium hydroxide catalyzes the formation of silver nanoparticles by abstracting the α-proton of galactose, causing the ring to open and forming the aldehyde functional group which readily reduces silver (I) to elemental silver. It is proposed that electron transfer proceeds through an associative mechanism between galactose and silver ions (Mukherjee M, Mahapatra A (2009) Colloid Surf A Phys Chem Eng Asp 350:1, incorporated herein by reference in its entirety). The reaction mechanism involves formation of an intermediate complex between silver(I) and galactose, which then dissociates in a slow step to give the products.

TABLE 2

The dependence of the reaction rate on [Ag+], [galactose] and [CTAB] = $1.0 \times 10^{-3}$ mol dm$^{-3}$ at T = 40.0° C.

| $10^3$ [OH$^-$] (mol dm$^{-3}$) | $10^5$ [Ag$^+$] (mol dm$^{-3}$) | $10^2$ [galactose] (mol dm$^{-3}$) | $10^3$ $k_{obs}$ (s$^{-1}$) |
|---|---|---|---|
| 10.0 | 5.00 | 0.5 | 1.15 |
|  |  | 0.75 | 1.87 |
|  |  | 1.00 | 3.23 |
|  |  | 1.25 | 4.18 |
|  |  | 1.50 | 4.67 |
|  |  | 2.00 | 5.50 |
| 2.50 |  | 1.00 | 0.83 |
| 5.00 |  |  | 1.24 |
| 7.50 |  |  | 1.63 |
| 12.50 |  |  | 6.21 |
| 15.00 |  |  | 8.93 |
| 10.00 | 2.50 | 1.00 | 3.37 |
|  | 3.75 |  | 3.56 |
|  | 6.25 |  | 3.49 |
|  | 7.50 |  | 3.70 |

TABLE 3

The variation of $k_1$ with hydroxide ion concentration at [Ag$^+$] = $5.0 \times 10^{-5}$ mol dm$^{-3}$, [galactose] = $1.0 \times 10^{-2}$ mol dm$^{-3}$, [CTAB] = $1.0 \times 10^{-3}$ mol dm$^{-3}$ and at different temperatures

| | 10 $k_1$ (dm$^3$ mol$^{-1}$ s$^{-1}$) | | | |
|---|---|---|---|---|
| $10^3$ [OH$^-$] (mol dm$^{-3}$) | T = 35.0° C. | T = 40.0° C. | T = 45.0° C. | T = 50.0° C. |
| 2.50 | 0.69 | 1.08 | 1.62 | 1.94 |
| 5.00 | 1.07 | 1.57 | 2.55 | 2.89 |
| 7.50 | 1.55 | 2.19 | 3.69 | 4.07 |
| 10.00 | 2.06 | 3.23 | 4.82 | 5.31 |
| 12.50 | 2.83 | 4.02 | 6.34 | 6.24 |
| 15.50 | 3.29 | 4.91 | 6.71 | 7.35 |

TABLE 4

The variation of hydroxide-independent rate constant $k_2$ and hydroxide-dependent rate constant $k_3$ with temperature

| Temp. (° C.) | $10^2$ $k_2$ (dm$^3$ mol$^{-1}$ s$^{-1}$) | $k_3$ (dm$^6$ mol$^{-2}$ s$^{-1}$) |
|---|---|---|
| 45.0 | 0.36 | 21.5 |
| 50.0 | 0.8 | 31.45 |
| 55.0 | 6.27 | 39.94 |
| 60.0 | 7.99 | 43.82 |

Equation (6) can be written as a complexation reaction between R—CHO and Ag$^+$ in the presence of OH$^-$. In the rate-determining step, the complex, R—COOAg, decomposes unimolecularly through a one electron redox process, giving Ag°, Eq. (8). In the following step, Ag° reacts with Ag$^+$ to yield a silver sol (Ag$_4^{2+}$) (Eq. 9). Thus, $$R\text{---}CHO + Ag^+ + OH^- \rightleftharpoons R\text{---}COOAg + H_2 K_1 \quad (6)$$

$$R\text{---}CHO + Ag^+ + H_2O \rightarrow R\text{---}COOH + Ag° + H_2 k_4 \quad (7)$$

$$R\text{---}COOAg \rightarrow R\text{---}COO^- + Ag° \, k_5 \quad (8)$$

$$2Ag° + 2Ag^+ \rightarrow Ag_4^{2+} (\text{fast}) \quad (9)$$

From the above mechanism, the rate law is given by:

$$\text{Rate} = k_4[R\text{---}CHO][Ag^+] + k_5[R\text{---}COOAg] \quad (10)$$

From Equilibrium (6), we obtain $$R\text{---}COOAg = K_1[R\text{---}CHO][Ag^+][OH^-] \quad (11)$$

Substitution of Eq. (11) into Eq. (10) gave Eq. (12).

$$\text{Rate} = k_4[R\text{---}CHO][Ag^+] + k_5 K_1[R\text{---}CHO][Ag^+][OH^-] \quad (12)$$

$$\text{Rate} = [R\text{---}CHO][Ag^+](k_4 + k_5 K_1[OH^-]) \quad (13)$$

hence $$k_{obs} = [R\text{---}CHO](k_4 + k_5 K_1[OH^-]) \quad (14)$$

Comparing Eqs. (14) and (5), we obtain $k_2 = k_4$ and $k_3 = K_2 k_5$. Equation (14) contains two terms: one first represents an [OH$^-$]-independent path, while the second represents an [OH$^-$]-dependent path.

The enthalpies and entropies of activation for the redox reaction of silver(1) with galactose were calculated. The positive ΔH* values are indicative the endothermic nature of the oxidation, while the negative values of ΔS* are consistent with an associative mechanism (Scott S L, Bakac A, Espenson J H (1992) J Am Chem Soc 114:4205, incorporated herein by reference in its entirety). Electron transfer reactions are generally characterized by positive values of ΔH* and large negative values of ΔS. The large negative value of ΔS* in the presence of micelles indicates that a more ordered activated complex is formed, while the high positive values of ΔH* indicate that the activated complex is highly solvated.

The invention claimed is:

1. A method of forming silver nanoparticles, comprising:
   reacting a silver(I) salt with a carbohydrate reductant in an aqueous solution comprising:
   the silver(I) salt;
   the carbohydrate reductant;
   water;
   an inorganic base; and
   a surfactant;
   wherein a concentration of the silver(I) salt in the aqueous solution ranges from 10-100 μM;
   wherein the reacting is performed at a temperature up to 60° C. to form the silver nanoparticles; and
   wherein the reacting is not performed with microwave irradiation.

2. The method of claim 1, wherein the reacting is performed for a period ranging from 1-40 minutes.

3. The method of claim 1, wherein the reacting is performed at a temperature ranging from 35-60° C.

4. The method of claim 1, wherein the silver(I) salt is silver(I) nitrate.

5. The method of claim 1, wherein a concentration of the carbohydrate reductant in the aqueous solution ranges from more than 5 times to 800 times relative to the concentration of the silver(I) salt in the aqueous solution.

6. The method of claim 1, wherein the carbohydrate reductant is a polyhydroxy aldehyde.

7. The method of claim 1, wherein the carbohydrate reductant is at least one selected from the group consisting of glucose, lactose, galactose and ribose.

8. The method of claim 1, wherein the carbohydrate reductant is galactose.

9. The method of claim 1, wherein a concentration of the inorganic base in the aqueous solution ranges from more than 10 times to 620 times relative to the concentration of the silver(I) salt in the aqueous solution.

10. The method of claim 1, wherein the inorganic base is at least one of an alkali metal hydroxide and an alkali metal carbonate.

11. The method of claim 1, wherein the inorganic base is sodium hydroxide.

12. The method of claim 1, wherein a concentration of the surfactant in the aqueous solution ranges from more than 10 times to 120 times relative to the concentration of the silver(I) salt in the aqueous solution.

13. The method of claim 1, wherein the surfactant is cetyltrimethylammonium bromide.

14. The method of claim 1, wherein the surfactant is sodium dodecyl sulfate.

15. The method of claim 1, wherein the aqueous solution further comprises a polymer, wherein a concentration of the polymer in the aqueous solution ranges from more than 0 ppm to 25 ppm.

16. The method of claim 1, wherein the silver nanoparticles are of at least one shape selected from the group consisting of a sphere, a spheroid and an ellipsoid.

17. The method of claim 15, wherein the polymer is chitosan, and an average distance between the silver nanoparticles in the aqueous solution is in a range of 7-30 nm.

18. The method of claim 16, wherein the silver nanoparticles have an average diameter of 10-50 nm.

19. A method of preparing a colloid, comprising:
    reacting a silver(I) salt with a carbohydrate reductant in an aqueous solution to form silver nanoparticles, wherein the aqueous solution comprises:
        the silver(I) salt;
        the carbohydrate reductant;
        water;
        an inorganic base;
        a surfactant; and
        optionally a polymer;
        wherein a concentration of the silver(I) salt in the aqueous solution ranges from 10-100 µM;
    isolating the silver nanoparticles; and
    suspending the silver nanoparticles in a solvent;
    wherein the reacting is performed at a temperature up to 60° C. to form the silver nanoparticles and
    wherein the reacting is not performed with microwave irradiation.

* * * * *